United States Patent
Kim et al.

(10) Patent No.: US 9,743,922 B2
(45) Date of Patent: Aug. 29, 2017

(54) WIRE KNOT DELIVERY DEVICE

(71) Applicants: Dongguk University Industry-Academic Cooperation Foundation, Seoul (KR); Pusan National University Industry-University Cooperation Foundation, Busan (KR)

(72) Inventors: Sung Min Kim, Goyang (KR); Hong Seok Lim, Seoul (KR); June Hong Kim, Busan (KR)

(73) Assignees: DONGGUK UNIVERSITY INDUSTRY-ACADEMIC COOPERATION FONDATION, Seoul (KR); PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 275 days.

(21) Appl. No.: 14/574,323

(22) Filed: Dec. 17, 2014

(65) Prior Publication Data
US 2015/0342600 A1    Dec. 3, 2015

(30) Foreign Application Priority Data

May 30, 2014 (KR) ........................ 10-2014-0066023

(51) Int. Cl.
*A61B 17/04* (2006.01)
*A61B 17/00* (2006.01)

(52) U.S. Cl.
CPC ...... *A61B 17/0469* (2013.01); *A61B 17/0485* (2013.01); *A61B 2017/00243* (2013.01); *A61B 2017/0474* (2013.01)

(58) Field of Classification Search
CPC ............ A61B 17/0459; A61B 17/0482; A61B 17/0483; A61B 17/0485; A61B 17/221; A61B 2017/0474; A61B 2017/0475; A61B 2017/0477; A61B 2017/2212
See application file for complete search history.

(56) References Cited

U.S. PATENT DOCUMENTS

| | | | | |
|---|---|---|---|---|
| 4,018,229 A | * | 4/1977 | Komiya | A61B 1/31 606/139 |
| 5,129,912 A | * | 7/1992 | Noda | A61B 17/0469 289/1.2 |
| 5,336,230 A | * | 8/1994 | Leichtling | A61B 17/0469 128/898 |

(Continued)

FOREIGN PATENT DOCUMENTS

WO    WO 2012/165552 A1    6/2012

*Primary Examiner* — Christopher L Templeton

(57) ABSTRACT

Disclosed is a wire knot delivery device, and more particularly, a wire knot delivery device for delivering and maintaining a knot of a medical wire in a medical procedure. The wire knot delivery device includes a first body, a second body parallel to the first body and moving relative to the first body, a first catching part connected to a side of the first body and caught by a side of the knot during the delivery of the knot, and a second catching part connected to a side of the second body and caught by another side of the knot during the delivery of the knot. As the second body moves, a distance between the first catching part and the second catching part is adjusted.

12 Claims, 17 Drawing Sheets

(56) References Cited

U.S. PATENT DOCUMENTS

| | | | | |
|---|---|---|---|---|
| 5,395,367 | A * | 3/1995 | Wilk | A61B 17/00234 606/1 |
| 5,499,991 | A * | 3/1996 | Garman | A61B 17/0483 606/148 |
| 5,569,269 | A * | 10/1996 | Hart | A61B 17/0469 112/169 |
| 5,618,290 | A * | 4/1997 | Toy | A61B 17/0469 606/139 |
| 5,817,112 | A * | 10/1998 | Christoudias | A61B 17/0469 606/139 |
| 5,993,466 | A * | 11/1999 | Yoon | A61B 17/062 606/144 |
| 6,126,665 | A * | 10/2000 | Yoon | A61B 17/0469 606/144 |
| 6,517,550 | B1 * | 2/2003 | Konya | A61B 17/32056 606/113 |
| 8,231,671 | B2 | 7/2012 | Kim | |
| 8,556,916 | B2 * | 10/2013 | Torrie | A61B 17/0469 606/148 |
| 9,468,743 | B2 * | 10/2016 | Karpiel | A61M 25/09041 |
| 2004/0092953 | A1 * | 5/2004 | Salameh | A61B 17/32056 606/113 |
| 2004/0127915 | A1 * | 7/2004 | Fleenor | A61B 17/0469 606/144 |
| 2004/0249393 | A1 * | 12/2004 | Weisel | A61B 17/06109 606/144 |
| 2007/0060930 | A1 * | 3/2007 | Hamilton | A61B 17/062 606/144 |
| 2007/0093859 | A1 * | 4/2007 | Phillips | A61B 17/0469 606/148 |
| 2007/0162048 | A1 * | 7/2007 | Quinn | A61B 17/12122 606/113 |
| 2008/0097484 | A1 | 4/2008 | Lim et al. | |
| 2009/0082787 | A1 * | 3/2009 | Pang | A61B 17/062 606/144 |
| 2010/0305517 | A1 * | 12/2010 | Horie | A61B 17/3478 604/272 |
| 2011/0106104 | A1 | 5/2011 | Dana et al. | |
| 2012/0289971 | A1 * | 11/2012 | Segermark | A61B 17/221 606/108 |
| 2013/0172913 | A1 | 7/2013 | Takahashi | |
| 2014/0012292 | A1 * | 1/2014 | Stewart | A61B 17/0485 606/148 |

* cited by examiner

WIRE KNOT DELIVERY DEVICE

CROSS-REFERENCE TO RELATED APPLICATION

The priority of Korean patent application No. 10-2014-0066023 filed on May 30, 2014, the disclosure of which is hereby incorporated in its entirety by reference, is claimed.

BACKGROUND

1. Field of the Invention

The present invention relates to a wire knot delivery device, and more particularly, to a wire knot delivery device for delivering and maintaining a knot of a medical wire in a medical procedure.

2. Background of the Invention

Medical wires, which are used in medical procedures, may be formed of metals or fiber materials such as nylon. Furthermore, medical wires may be formed of any materials, provided that the materials are not harmful to the human body.

Medical wires can be variously used in medical procedures. For example, the tension of a medical wire may be used by forming a knot. Such a method is disclosed in detail in patent document 1 Patent document 1 discloses mitral cerclage coronary sinus annuloplasty (MVA) in which circular pressure is applied around the mitral annulus (MA).

Also, patent document 1 discloses a technology of forming a knot of a cerclage suture as a medical wire. Referring to patent document 1, a wire knot delivery mechanism is used to form a knot of a cerclage suture. FIGS. 1a to 1f are views illustrating a use of a wire knot delivery mechanism in the conventional art.

Referring to FIG. 1a, two strands of the cerclage suture 10 extending out of a human body are inserted into a through hole formed at an end of a wire knot delivery mechanism 30 to form a knot, and then, an end of the cerclage suture 10 is passed through an inner cavity of the wire knot delivery mechanism 30. After that, the wire knot delivery mechanism 30 is pushed to the heart of the human body such that the end of the wire knot delivery mechanism 30 is disposed on an upper end part of a tissue protection tube 20. As such, the wire knot delivery mechanism 30 delivers the knot while keeping the knot from tightening. After that, tension is applied to the cerclage suture 10 and is appropriately adjusted until mitral regurgitation stops. That is, referring to FIG. 1b, the strands of the cerclage suture 10 are appropriately pulled or released outside of the human body to adjust the tension of the cerclage suture 10 until the mitral regurgitation stops. When the tension reaches an appropriate value, an opening and closing part 32 of the wire knot delivery mechanism 30 is opened. To this end, the opening and closing part 32 may be cut using a cutter, but a method of opening the opening and closing part 32 is not limited thereto. After that, referring to FIG. 1d, when the cerclage suture 10 is pulled outside of the human body, the knot, kept from tightening by the opening and closing part 32, tightens to fix the tension of the cerclage suture 10. After that, referring to FIG. 1e, the cerclage suture 10 is cut at a predetermined distance from the knot by using a cutter, and the remainder of the cerclage suture 10 and the wire knot delivery mechanism 30 are taken out of the human body. Accordingly, referring to FIG. 1f, the end of the cerclage suture 10 is fixed as a knot 12.

However, such a conventional method of delivering a knot of a medical wire, a method of cutting the medical wire, and a method of forming the knot have the following limitations.

Conventional wire knot delivery mechanisms cannot instantly tighten a knot of a medical wire even after adjustment of tension of the medical wire is completed since an opening and closing part is not removed. In addition, when the opening and closing part is cut to tighten the knot, the adjustment of the tension may be changed. Accordingly, it may be difficult to accurately adjust the tension of the medical wire.

In addition, conventional wire knot delivery mechanisms have a structure in which while a knot of a medical wire is delivered, friction or resistance increases between the knot and an opening and closing part. Thus, it is difficult to efficiently deliver the knot.

In addition, since a loop size of the knot during the delivery of the knot depends on only the size of the opening and closing part, it is difficult to change the loop size according to the size of a blood vessel during the delivery of the knot.

In addition, after the delivery of the knot is completed, the knot cannot be completed without cutting the opening and closing part. Since the opening and closing part is finally moved to a location close to the heart of a human body in the blood vessel, a cutting tool should be also moved to the location close to the heart in the blood vessel to cut the opening and closing part. This may impose a heavy burden on a cutting process.

CITED DOCUMENT

[Patent Document 1] U.S. Pat. No. 8,231,671

SUMMARY

Various embodiments of the invention are directed to providing a wire knot delivery device, which precisely adjusts tension of a medical wire and completes the adjustment.

In addition, various embodiments of the invention are directed to providing a wire knot delivery device having a structure that decreases friction or resistance while delivering a knot of a medical wire, thus facilitating the delivery of the knot.

In addition, various embodiments of the invention are directed to providing a wire knot delivery device that adjusts a loop size of a knot of a medical wire while delivering the knot.

In addition, various embodiments of the invention are directed to providing a wire knot delivery device that finishes a medical procedure for forming a knot of a medical wire, without inserting a cutting mechanism into a deep part of a blood vessel after completing a delivery of the knot.

According to an embodiment of the present invention, a wire knot delivery device for delivering and maintaining a knot of a medical wire includes: a first body; a second body parallel to the first body and moving relative to the first body; a first catching part connected to a side of the first body and caught by a side of the knot during the delivery of the knot; and a second catching part connected to a side of the second body and caught by another side of the knot during the delivery of the knot, wherein as the second body moves, a distance between the first catching part and the second catching part is adjusted.

DETAILED DESCRIPTION

Hereinafter, exemplary embodiments of the present invention will be described in detail with reference to the accompanying drawings. However, the present invention is not limited to the following embodiments.

Embodiment

Figure 1:
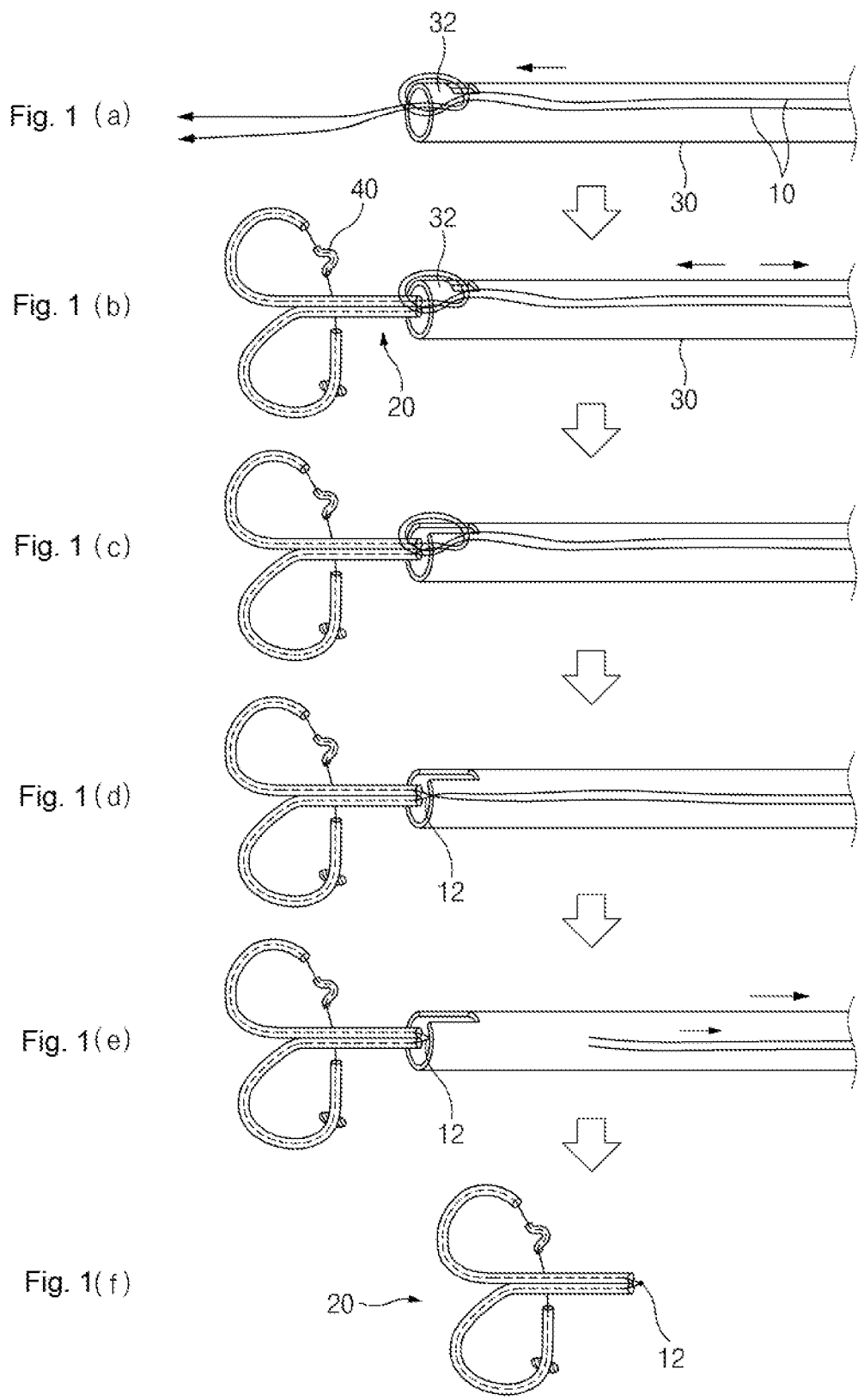
FIGS. 1a to 1f are views illustrating a use of a wire knot delivery mechanism in the conventional art.
Figure 2:
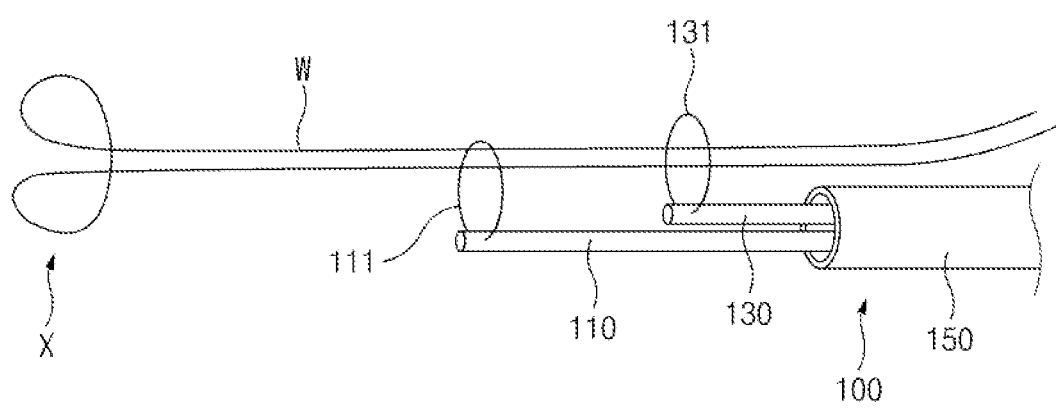
FIG. 2 is a view illustrating a state in which a wire knot delivery device is ready to deliver a knot according to an embodiment of the present invention.
Figure 3:
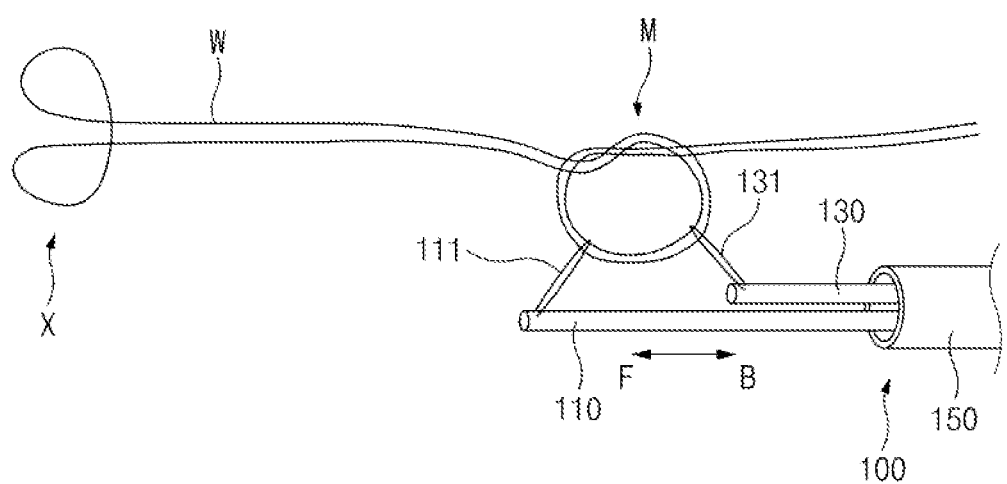
FIG. 3 is a view illustrating a knot of a medical wire and a first mode of the wire knot delivery device of FIG. 2.
Figure 4:
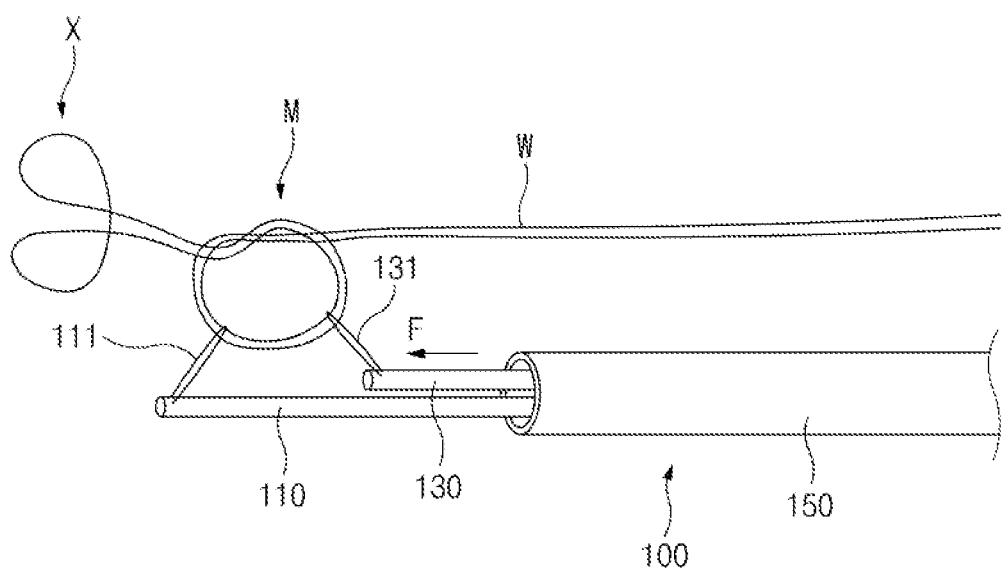
FIG. 4 is a view illustrating the knot delivered by the wire knot delivery device of FIG. 3.
Figure 5:
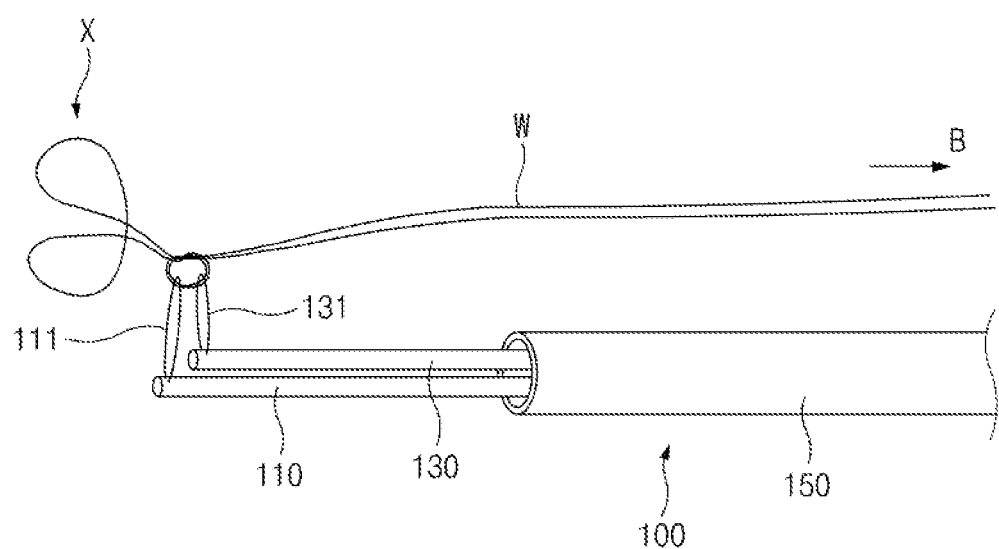
FIG. 5 is a view illustrating a second mode of the wire knot delivery device and a state in which the knot tightens.

FIG. 2 is a view illustrating a state in which a wire knot delivery device is ready to deliver a knot according to an embodiment of the present invention. FIG. 3 is a view illustrating a knot of a medical wire and a first mode of the wire knot delivery device of FIG. 2. FIG. 4 is a view illustrating the knot delivered by the wire knot delivery device of FIG. 3. FIG. 5 is a view illustrating a second mode of the wire knot delivery device and a state in which the knot tightens.

Referring to FIGS. 2 to 5, a wire knot delivery device will now be described in detail according to the current embodiment.

A wire knot delivery device 100 according to the current embodiment, which delivers and maintains a knot of a wire W for a medical procedure, includes a first body 110, a second body 130, a first catching part 111, and a second catching part 131. The second body 130 is parallel to the first body 110. The second body 130 may slide relative to the first body 110.

The first catching part 111 and the second catching part 131 may have a string shape that may be caught by the wire W. The string shape is flexible and is appropriate to decrease the coefficient of friction, so as to decrease friction or resistance generated during the delivery of the knot of the wire W.

The first catching part 111 may be connected to a side of the first body 110, and the second catching part 131 may be connected to a side of the second body 130. As the second body 130 moves relative to the first body 110, a distance between the first catching part 111 and the second catching part 131 may be adjusted. A first mode is a state that the first catching part 111 and the second catching part 131 are spaced apart from each other, and a second mode is a state that the first catching part 111 and the second catching part 131 are adjacent to each other.

The wire knot delivery device 100 may further include a main guide part 150 that guides a movement of the second body 130 such that the second body 130 can slide relative to the first body 110. The main guide part 150 may have a tube shape that can be inserted in a blood vessel. In this case, a wire knot can be efficiently delivered in a deep part of a human body.

The first body 110 and the second body 130 may be inserted in the main guide part 150. In this case, the main guide part 150 and the first body 110 may be fixed to each other such that the main guide part 150 and the first body 110 are prevented from moving relative to each other. Thus, when the second body 130 moves relative to the first body 110, the main guide part 150 stably guides the second body 130.

A method of delivering the knot of the wire W by using the wire knot delivery device 100 will now be described according to the current embodiment.

Referring to FIG. 2, the wire knot delivery device 100 is ready to deliver the knot (in operation S10). At this point, a part X to be medically treated may be in the body of a patient, and the wire knot delivery device 100 may be out of the body. First, to deliver the knot, the wire W extending from the part X may be passed through holes of the first catching part 111 and the second catching part 131 (in operation S20).

Referring to FIG. 3, the second body 130 may be moved in a direction B to form the first mode that the first catching part 111 and the second catching part 131 are spaced apart from each other. The wire W may be formed into a circular shape to form the knot (in operation S30). At this point, the size of a wire knot M having a circular shape may be determined according to a distance between the first catching part 111 and the second catching part 131. The distance between the first catching part 111 and the second catching part 131 may be appropriately adjusted according to the size of a blood vessel as a passage along which the wire knot M is delivered.

After the wire knot M having the circular shape is formed, the wire knot delivery device 100 may be moved in a direction F to deliver the wire knot M. While the wire knot delivery device 100 is moved, the first mode is maintained to keep the wire knot M from tightening during the delivery of the wire knot M. When the wire knot M is delivered, the first catching part 111 may be caught by a side of the wire knot M, and the second catching part 131 may be caught by another side of the wire knot M.

Referring to FIG. 4, the wire knot delivery device 100 is moved in the direction F, to thereby deliver the wire knot M to the part X (in operation S40). After that, a hand of a medical operator holds the wire knot delivery device 100, and the other hand appropriately pulls the wire W in the direction B, thereby appropriately adjusting tension of the wire W (in operation S50). At this point, if necessary, the medical operator may appropriately move the second body 130 in the direction F to adjust the tension of the wire W.

Referring to FIG. 5, when the adjustment of the tension of the wire W is completed, the medical operator may form the second mode that the first catching part 111 and the second catching part 131 are adjacent to each other. At this point, the medical operator may tighten the wire knot M (in operation S60). Accordingly, the tension of the wire W may be fixed. After that, an unnecessary portion of the wire W may be cut and removed (in operation S70).

As such, the wire knot delivery device 100 may complete the adjustment of the tension of the wire W, and simultaneously, tighten the wire knot M of the wire W. Accordingly, the wire knot delivery device 100 precisely adjust the tension of the wire W and complete the adjustment.

Another Embodiment

Figure 6:
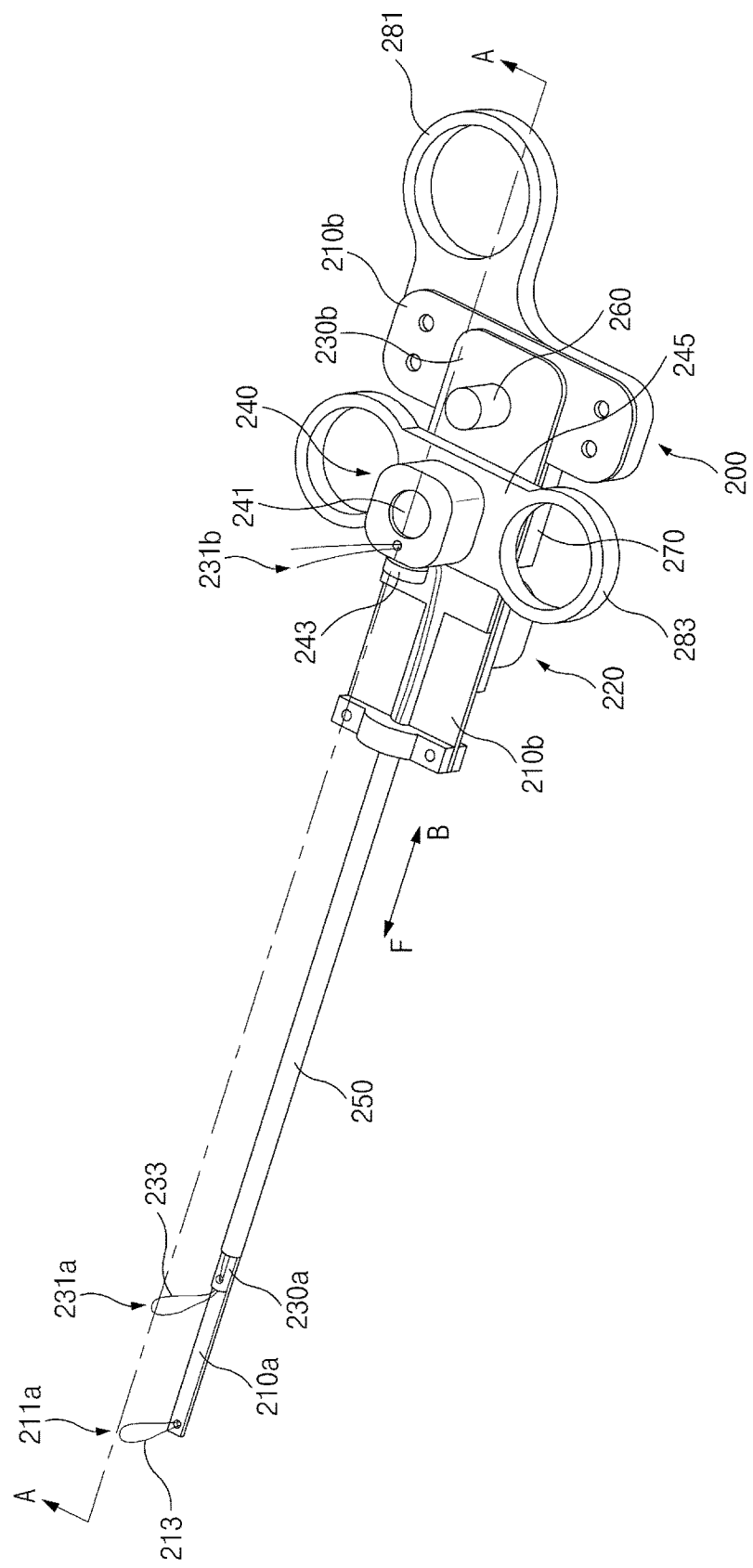
FIG. 6 is a perspective view illustrating the upper part of a wire knot delivery device in a first mode according to another embodiment of the present invention.
Figure 7:
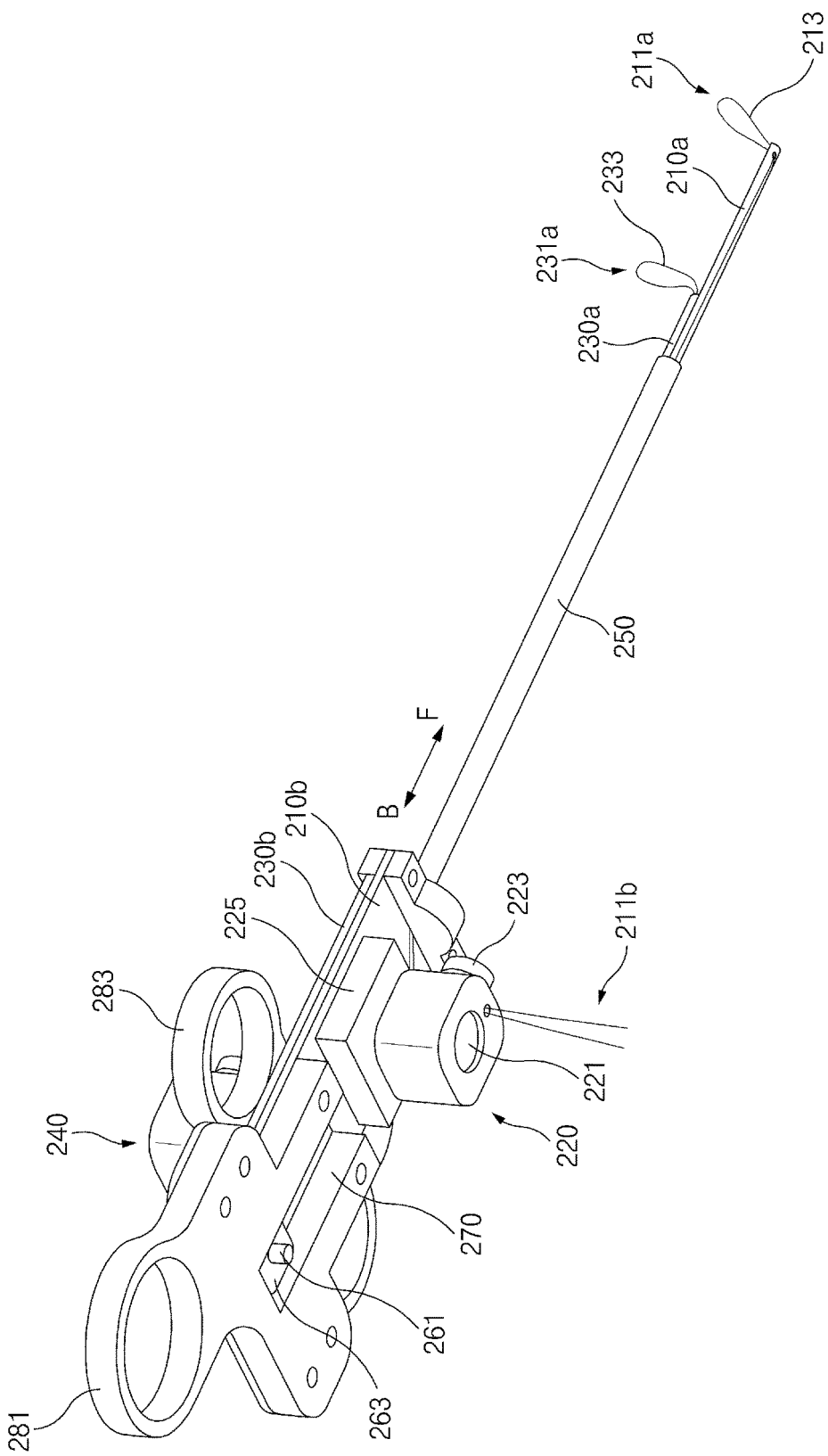
FIG. 7 is a perspective view illustrating the lower part of the wire knot delivery device in the first mode of FIG. 6.
Figure 8:
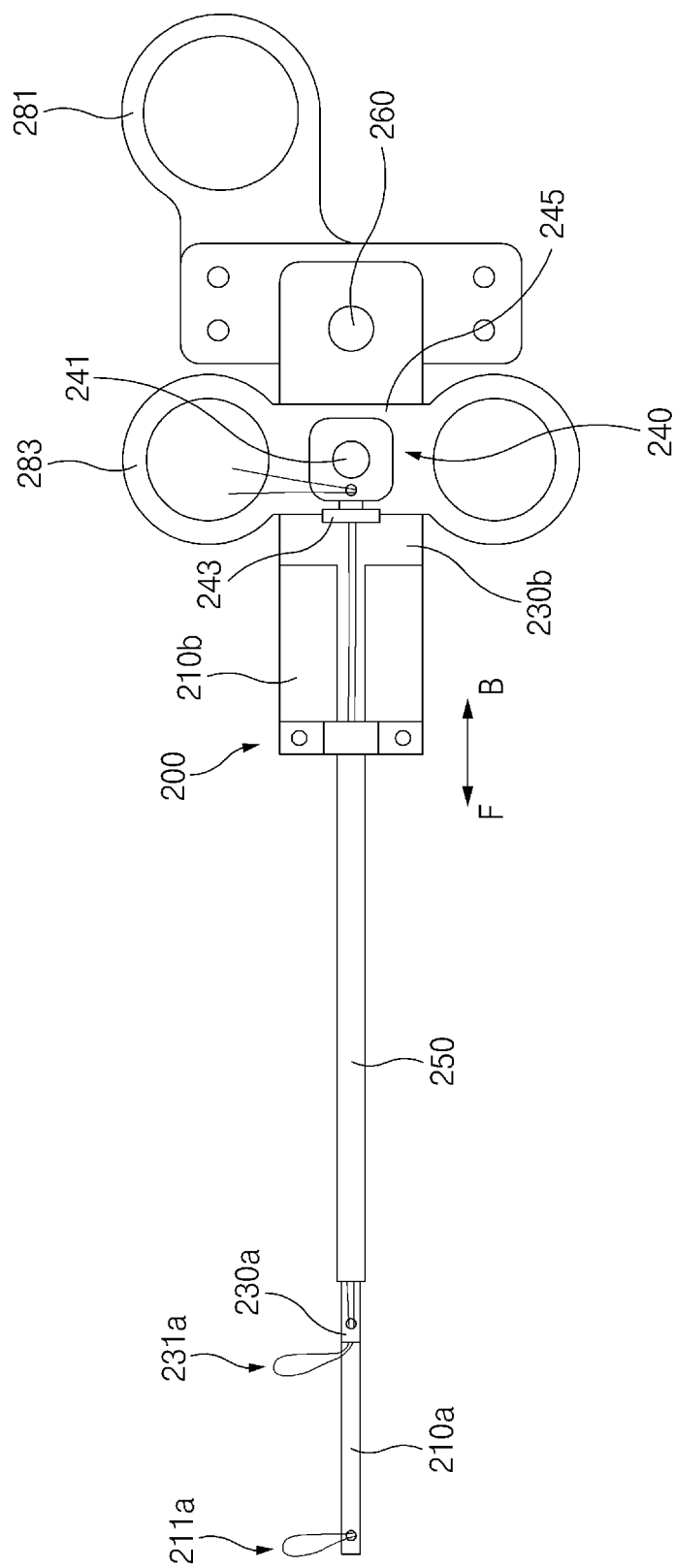
FIG. 8 is a plan view illustrating the wire knot delivery device of FIG. 6.
Figure 9:
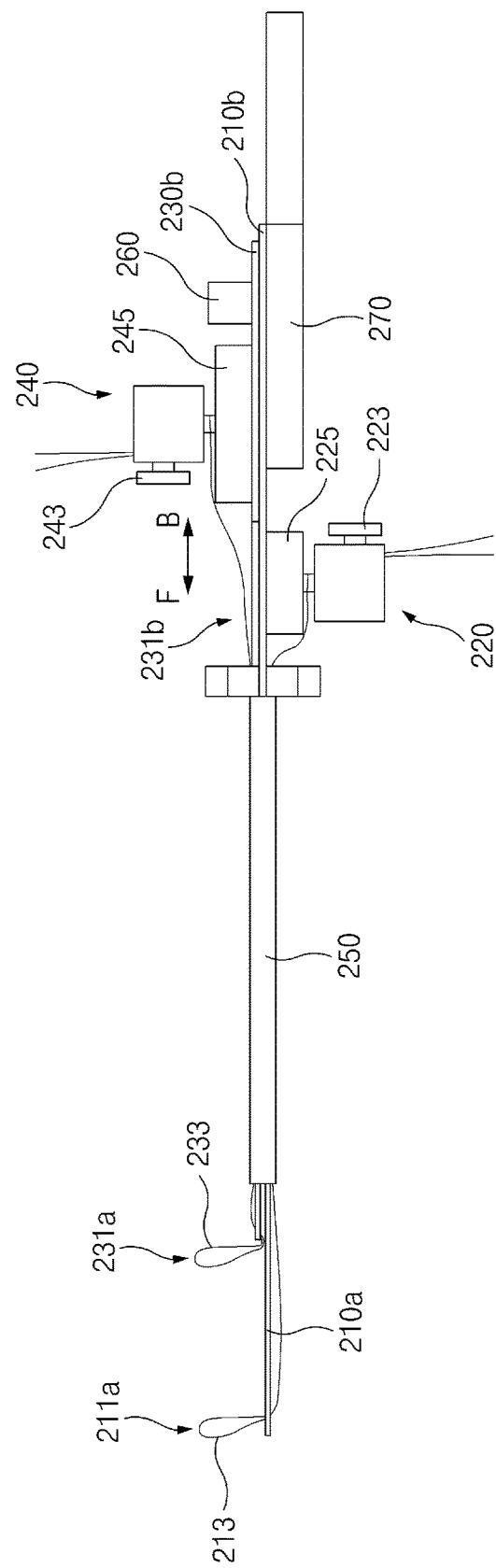
FIG. 9 is a side view illustrating the wire knot delivery device of FIG. 6.
Figure 10:
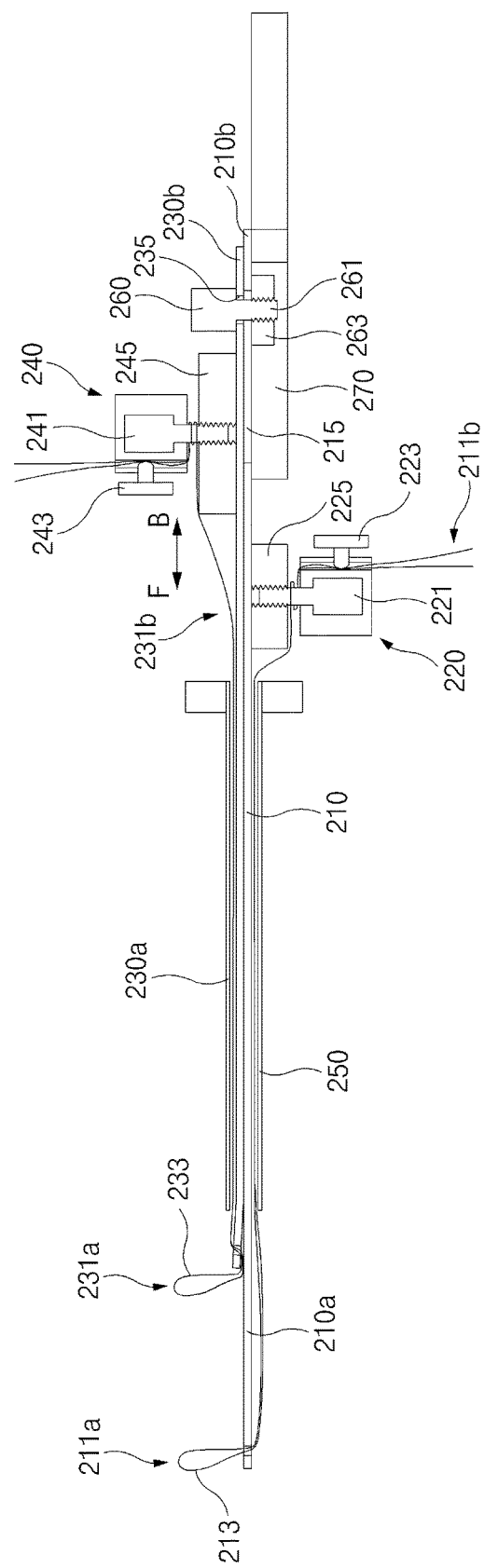
FIG. 10 is a cross-sectional view taken along line A-A of FIG. 6.
Figure 11:
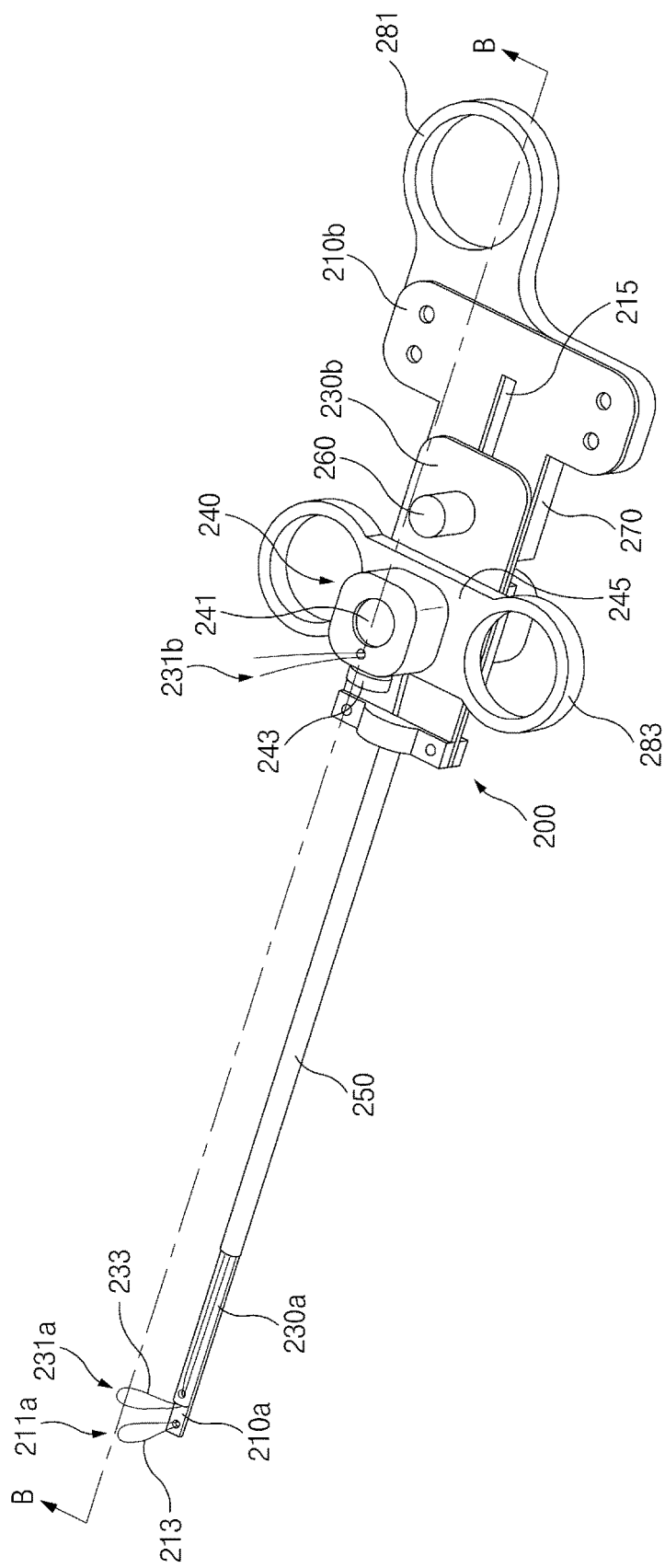
FIG. 11 is a perspective view illustrating the upper part of the wire knot delivery device of FIG. 6 in a second mode.
Figure 12:
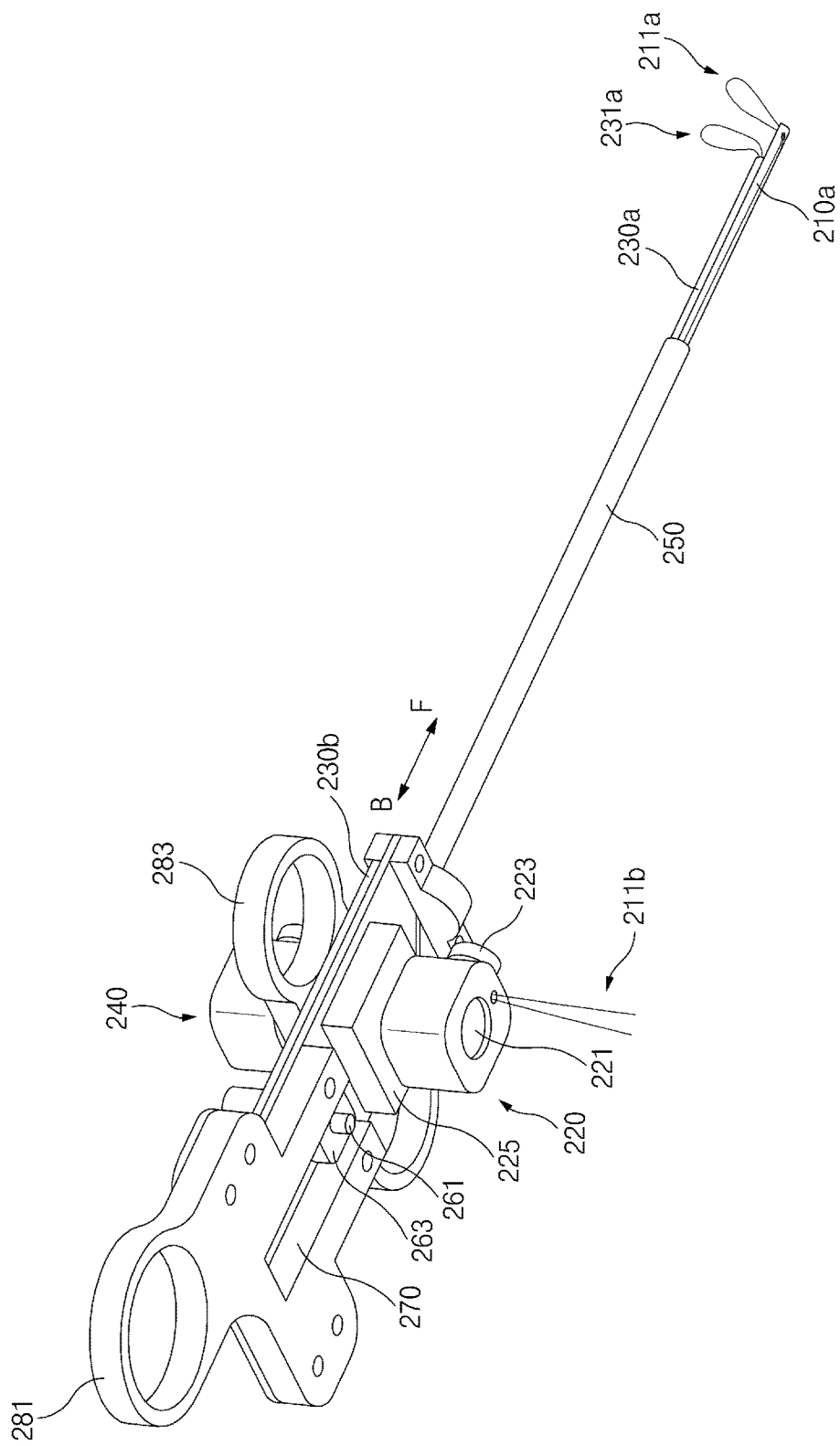
FIG. 12 is a perspective view illustrating the lower part of the wire knot delivery device in the second mode of FIG. 11.
Figure 13:
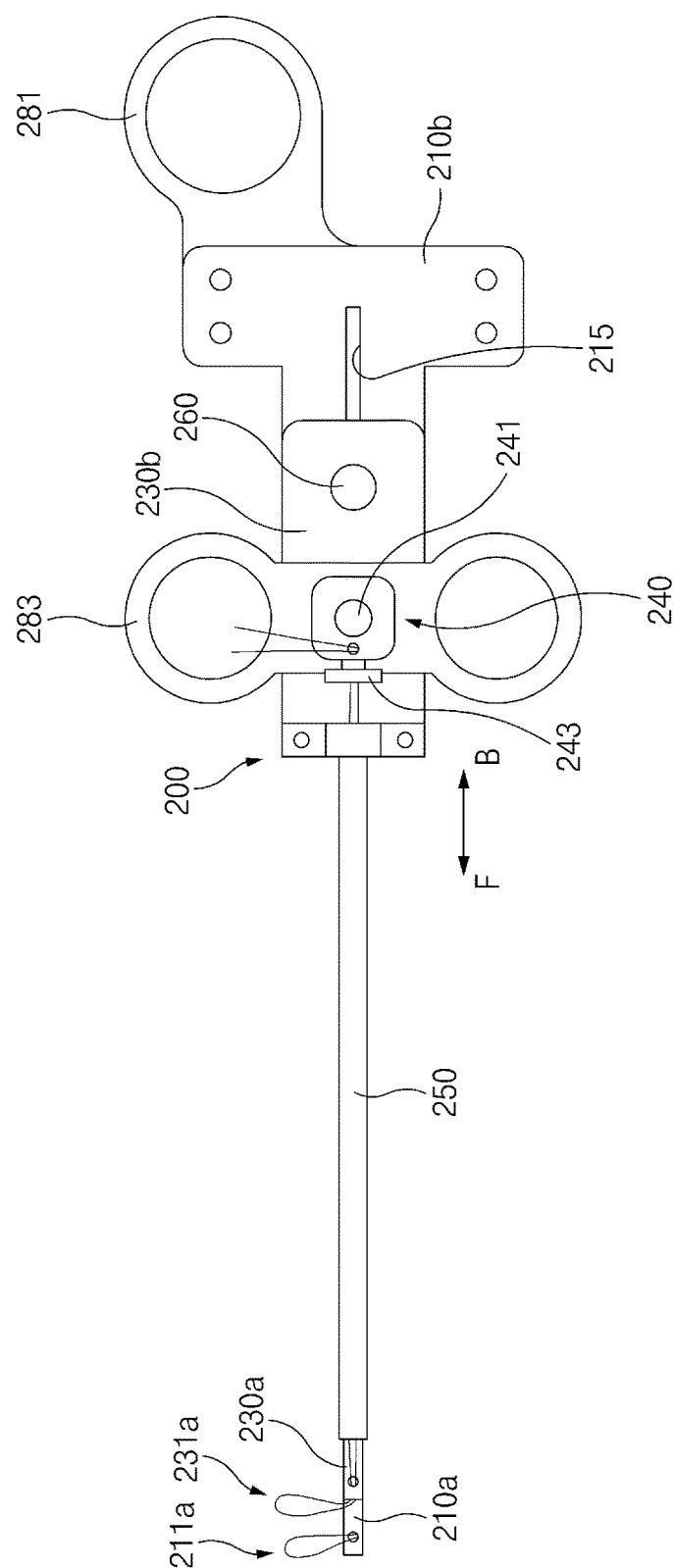
FIG. 13 is a plan view illustrating the wire knot delivery device of FIG. 11.
Figure 14:
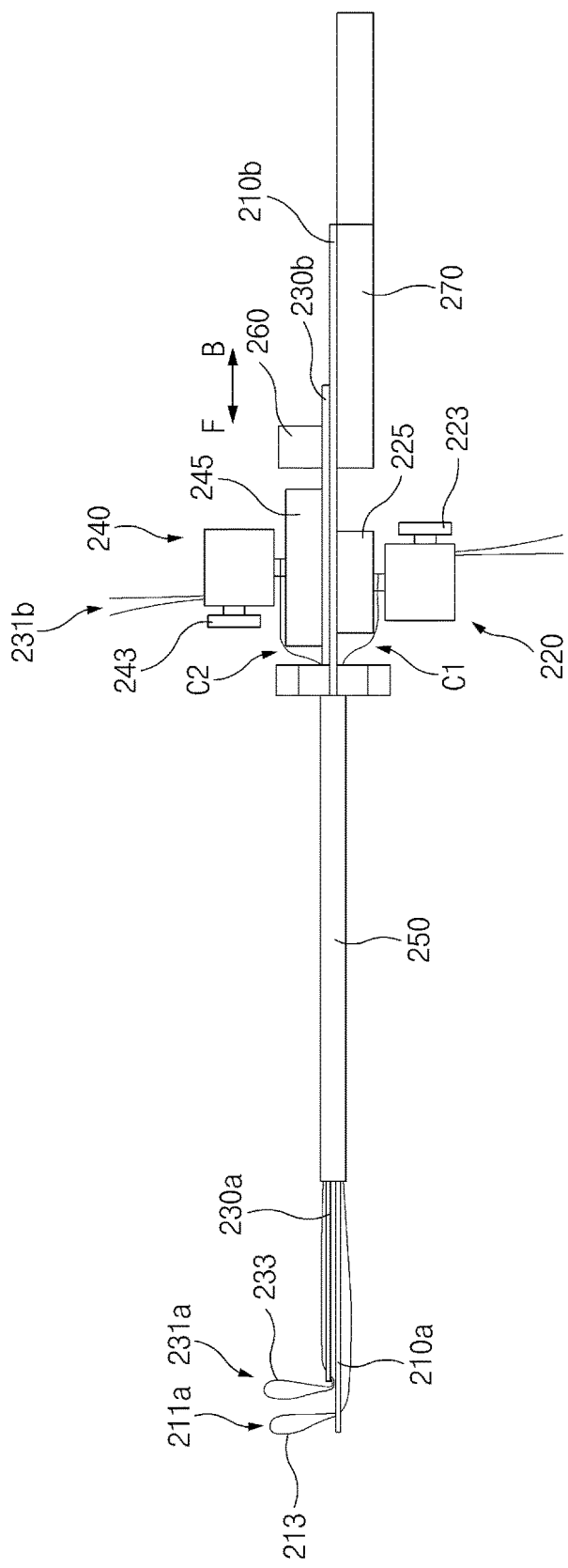
FIG. 14 is a side view illustrating the wire knot delivery device of FIG. 11.
Figure 15:
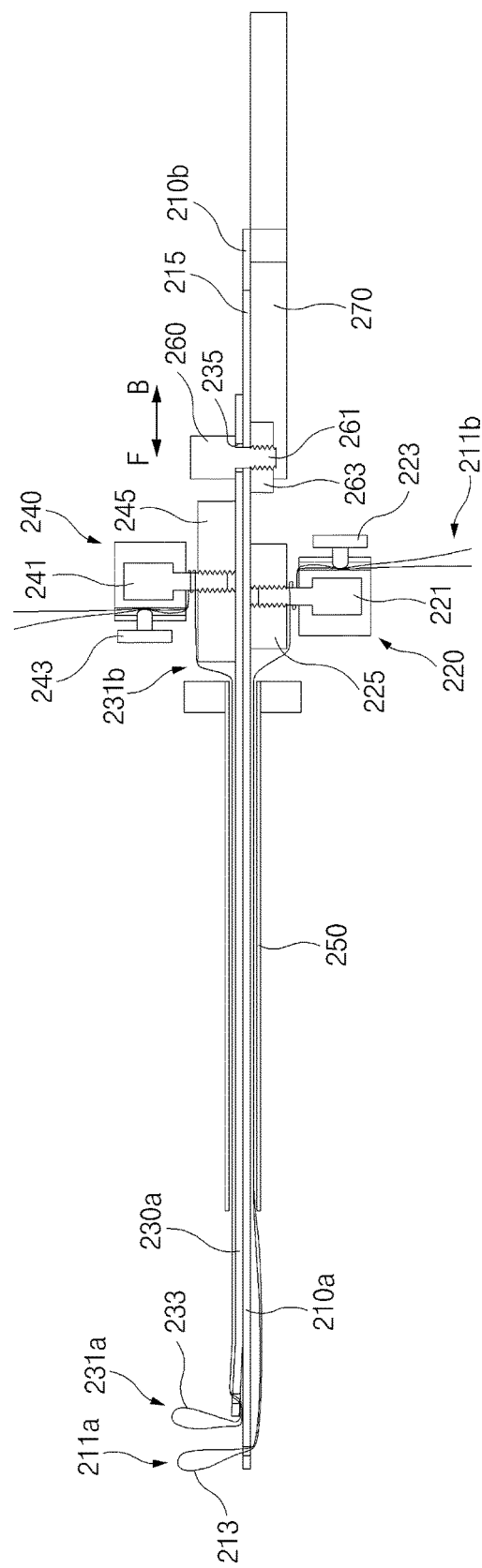
FIG. 15 is a cross-sectional view taken along line B-B of FIG. 11.
Figure 16:
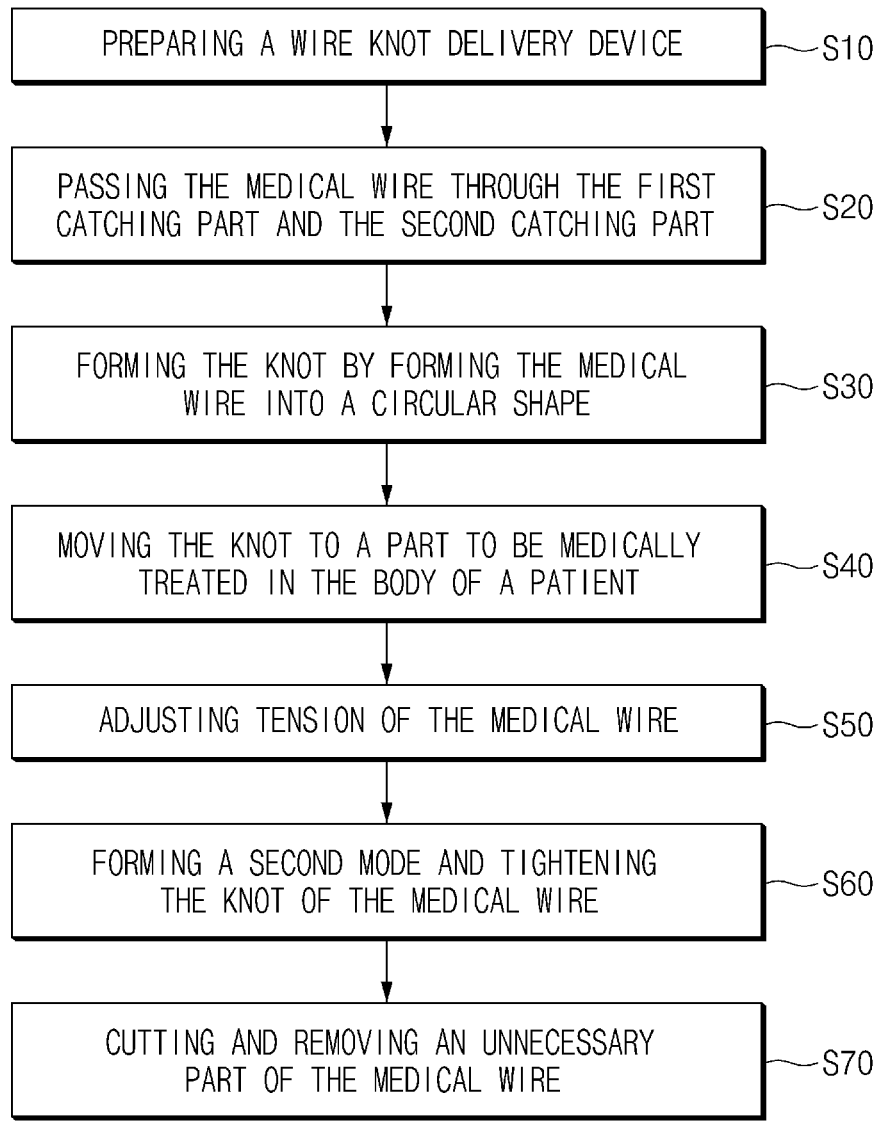
FIG. 16 is a flow chart representing a wire know delivery method.
Figure 17:
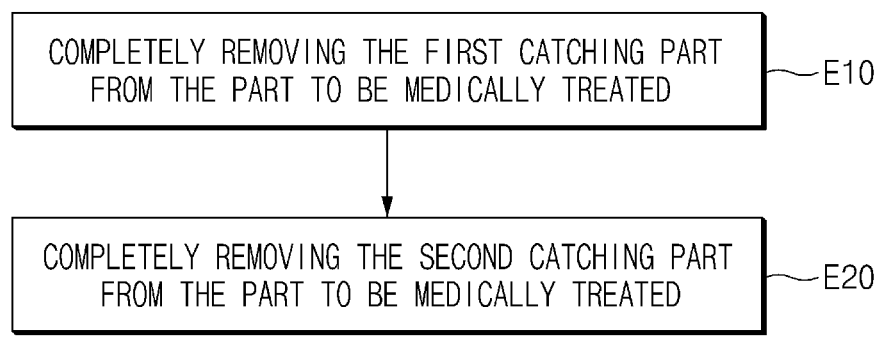
FIG. 17 is a flow chart representing a step of a wire knot delivery method.

FIG. 6 is a perspective view illustrating the upper part of a wire knot delivery device in a first mode according to another embodiment of the present invention. FIG. 7 is a perspective view illustrating the lower part of the wire knot delivery device in the first mode according to the current embodiment. FIG. 8 is a plan view illustrating the wire knot delivery device of FIG. 6. FIG. 9 is a side view illustrating the wire knot delivery device of FIG. 6. FIG. 10 is a cross-sectional view taken along line A-A of FIG. 6. FIG. 11 is a perspective view illustrating the upper part of the wire knot delivery device in a second mode according to the current embodiment. FIG. 12 is a perspective view illustrating the lower part of the wire knot delivery device in the second mode according to the current embodiment. FIG. 13 is a plan view illustrating the wire knot delivery device of FIG. 11. FIG. 14 is a side view illustrating the wire knot delivery device of FIG. 11. FIG. 15 is a cross-sectional view taken along line B-B of FIG. 11.

A wire knot delivery device according to the current embodiment may have a configuration similar to that of the wire knot delivery device according to the previous embodiment. However, the wire knot delivery device according to the current embodiment is different from the wire knot delivery device according to the previous embodiment in that the former includes an additional configuration for providing an advanced function.

A wire knot delivery device will now be described with reference to FIGS. 6 to 15 according to the current embodiment.

Referring to FIGS. 6, 7, 9, and 10, a wire knot delivery device 200 according to the current embodiment may include includes a first body 210a and 210b, a second body 230a and 230b, a first catching part 213, and a second catching part 233, which are similar to those of the previous embodiment.

However, the current embodiment is more specified than the previous embodiment. The first body 210a and 210b may include a first stick part 210a and a first plate part 210b. The first stick part 210a and the first plate part 210b are integrally formed as a single piece and are portions of the first body 210a and 210b.

The first stick part 210a is the part of the first body 210a and 210b oriented in a direction F, which catches a medical wire, and the first plate part 210b is a plate-shaped part opposite to the first stick part 210a. In a same manner, the second body 230a and 230b may include a second stick part 230a and a second plate part 230b.

The first catching part 213 and the second catching part 233 may have a string shape. The first catching part 213 may include a first catching part loop 211a and a first rear string 211b. The first catching part loop 211a and the first rear string 211b are integrally formed as a single piece and are portions of the first catching part 213.

In particular, the first catching part 213 has a string shape extending from the side F of the first body 210a and 210b to a side B and includes: the first catching part loop 211a at the side F of the first body 210a and 210b to catch a medical wire; and the first rear string 211b at the side B of the first body 210a and 210b opposite to the first catching part loop 211a, that is, adjacent to the first plate part 210b. In a same manner, the second catching part 233 includes a second catching part loop 231a and a second rear string 231b.

The wire knot delivery device 200 may include a first adjustment part 220 and a second adjustment part 240 for adjusting the length or size of the first catching part 213 and the second catching part 233. The first adjustment part 220 may be coupled to the first body 210a and 210b, and the second adjustment part 240 may be coupled to the second body 230a and 230b. In particular, the first adjustment part 220 may be coupled to the first plate part 210b of the first body 210a and 210b at the side B, and the second adjustment part 240 may be coupled to the second plate part 230b of the second body 230a and 230b at the side B.

The first adjustment part 220 may include a first rotation member 221, a first press member 223, and a first base member 225.

The first base member 225 may be coupled to the first body 210a and 210b, and the first rotation member 221 may be screwed to the first base member 225. Accordingly, the first rotation member 221 may be coupled to the first body 210a and 210b through the first base member 225.

However, the coupling of the first rotation member 221 to the first body 210a and 210b is not limited thereto. The first rotation member 221 may be directly screwed to the first body 210a and 210b. In this case, the first base member 225 may be removed from the first adjustment part 220. That is, the first adjustment part 220 may include only the first rotation member 221 and the first press member 223 to adjust the length or size of the first catching part 213.

The first rotation member 221 may wind the first catching part 213. The first catching part 213 may have a string shape extending from the side F of the first body 210a and 210b to the side B, and the first rotation member 221 may rotate to wind the first rear string 211b disposed at the side B of the first body 210a and 210b. An end part of the first catching part 213 having a string shape, that is, the first rear string 211b may be wound around a rotation shaft part of the first rotation member 221 rotatably screwed to the first base member 225.

The first press member 223 may be screwed to the first rotation member 221 to press the first rear string 211b to a rotation shaft of the first rotation member 221. The first rear string 211b may be caught between the first press member 223 and the rotation shaft part of the first rotation member 221 and be thus fixed therebetween.

After the first rear string 211b is fixed by the first press member 223, when the first rotation member 221 is rotated to wind the first rear string 211b, the first catching part 213 may be moved to the side B of the first body 210a and 210b to decrease the size of the first catching part loop 211a. On the contrary, when the first rotation member 221 is rotated in a direction of unwinding the first rear string 211b, the first catching part 213 may be moved to the side F of the first body 210a and 210b to increase the size of the first catching part loop 211a.

When the size of the first catching part loop 211a is increased, a medical wire can be efficiently inserted into the first catching part loop 211a in a preparation stage. On the contrary, when the size of the first catching part loop 211a is decreased, a knot of a medical wire which has a circular shape is more effectively prevented from tightening while the knot is delivered to a part to be medically treated.

The second adjustment part 240 corresponding to the first adjustment part 220 may include a second rotation member 241, a second press member 243, and a second base member 245.

As in the first adjustment part 220, the second rotation member 241 may be coupled to the second body 230a and 230b through the second base member 245.

However, also as in the first adjustment part 220, the second rotation member 241 may be directly screwed to the second body 230a and 230b. In this case, the second base member 245 may be removed from the second adjustment part 240, and the second adjustment part 240 may include only the second rotation member 241 and the second press member 243 to adjust the length or size of the second catching part 233.

The second rotation member 241 of the second adjustment part 240 may wind the second catching part 233. The second catching part 233 may have a string shape extending over the second body 230a and 230b from the side F to the side B, and the second rotation member 241 may rotate to wind the second rear string 231b disposed at the side B on the second body 230a and 230b. An end part of the second catching part 233 having a string shape, that is, the second rear string 231b may be wound around a lower rotation shaft part of the second rotation member 241 rotatably screwed to the second base member 245.

The second press member 243 may be screwed to the second rotation member 241 to press the second rear string 231b to a rotation shaft of the second rotation member 241. The second rear string 231b may be caught between the second press member 243 and the lower rotation shaft part of the second rotation member 241 and be thus fixed therebetween.

After the second rear string 231b is fixed by the second press member 243, when the second rotation member 241 is rotated to wind the second rear string 231b, the second catching part 233 may be moved to the side B over the second body 230a and 230b to decrease the size of the second catching part loop 231a. On the contrary, when the second rotation member 241 is rotated in a direction of unwinding the second rear string 231b, the second catching part 233 may be moved to the side F over the second body 230a and 230b to increase the size of the second catching part loop 231a.

When the size of the second catching part loop 231a is increased, a medical wire can be efficiently inserted into the second catching part loop 231a in a preparation stage. On the contrary, when the size of the second catching part loop 231a is decreased, a knot of a medical wire which has a circular shape is more effectively prevented from tightening while the knot is delivered to a part to be medically treated.

Referring to FIGS. 6 to 10, the wire knot delivery device 200 is in a first mode that the first catching part 213 and the second catching part 233 are spaced apart from each other. Referring to FIGS. 11 to 15, the wire knot delivery device 200 is in a second mode that the first catching part 213 and the second catching part 233 are adjacent to each other. In particular, the first catching part loop 211a and the second catching part loop 231a may be spaced apart from each other in the first mode, and the first catching part loop 211a and the second catching part loop 231a may be adjacent to each other in the second mode.

Referring to FIGS. 6 to 10, the second body 230a and 230b is moved to the side B relative to the first body 210a and 210b in the first mode.

In this case, the second stick part 230a is moved to the side B relative to the first stick part 210a, and the second plate part 230b is also moved to the side B relative to the first plate part 210b.

Accordingly, the first catching part loop 211a and the second catching part loop 231a are spaced apart from each other. In this state, a medical wire may be inserted into the first catching part loop 211a and the second catching part loop 231a. A circular knot may be formed from the medical wire inserted in the first catching part loop 211a and the second catching part loop 231a, as illustrated in FIG. 3.

After that, the first rotation member 221 and the second rotation member 241 may be rotated to decrease the sizes of the first catching part loop 211a and the second catching part loop 231a. At this point, the second plate part 230b may be appropriately moved to the side F or B to appropriately adjust the size of the circular knot of the medical wire. When the adjustment is completed, the circular knot is delivered to a part to be medically treated. At this point, the first body 210a and 210b and the second body 230a and 230b may not be moved relative to each other. To this end, the first plate part 210b and the second plate part 230b may be fixed to be prevented from being moved relative to each other.

A coupling member head 260, a coupling member rod 261, and a coupling member 263 may prevent the first body 210a and 210b and the second body 230a and 230b from being moved relative to each other.

Referring to FIGS. 10, 11, 12, and 15, the first body 210a and 210b may include a first through hole 215 passing through the first plate part 210b of the first body 210a and 210b, and the second body 230a and 230b may include a second through hole 235 passing through the second plate part 230b of the second body 230a and 230b and communicating with the first through hole 215. The coupling member rod 261 extending from the coupling member head 260 may be inserted in the second through hole 235 and the first through hole 215. The coupling member 263 may be coupled to an end part of the coupling member rod 261 opposite to the coupling member head 260.

Referring to FIG. 10, the coupling member rod 261 and the coupling member 263 may be coupled to each other as a bolt and a nut. The coupling member head 260 has a size to be prevented from passing through the second through hole 235. Thus, when the coupling member 263 is rotated and tightened, the coupling member head 260 and the coupling member 263 approach each other. Accordingly, the first plate part 210b and the second plate part 230b are pressed to be brought into tight contact with each other. The pressing may fix and prevent the first body 210a and 210b and the second body 230a and 230b from moving relative each other. As a result, the first stick part 210a and the second stick part 230a are fixed and prevented from moving relative to each other.

The first body 210a and 210b and the second body 230a and 230b may be fixed and prevented from moving relative to each other, by rotating and tightening the coupling member 263. Alternatively, the first body 210a and 210b and the second body 230a and 230b may be fixed and prevented from moving relative to each other, by rotating the coupling member head 260 in a screw tightening direction, without rotating the coupling member 263.

The coupling member head 260 is rotated in a screw loosening direction and is released in order to move the second body 230a and 230b relative to the first body 210a and 210b. In this case, the second plate part 230b is allowed to move relative to the first plate part 210b. Accordingly, the second body 230a and 230b is allowed to move relative to the first body 210a and 210b. As a result, the second body 230a and 230b is allowed to move between the first and second modes.

When the second body 230a and 230b is moved, the second body 230a and 230b may be guided by a main guide part 250. The guiding of the main guide part 250 may be performed in a manner as described according to the previous embodiment.

Referring to FIGS. 6, 10, 11, and 15, the second through hole 235 has a size corresponding to a diameter of the coupling member rod 261. Thus, when the second body 230a and 230b moves between the first and second modes, the coupling member rod 261 moves together with the second body 230a and 230b and is inserted in the second through hole 235.

At this point, since the first through hole 215 is elongated in a moving direction of the second body 230a and 230b, the coupling member rod 261 slides in a longitudinal direction of the first through hole 215, and the first through hole 215 guides the sliding of the coupling member rod 261.

Referring to FIGS. 7, 10, 12, and 15, when the coupling member rod 261 moves, the coupling member 263 moves together with the coupling member rod 261. At this point, an auxiliary guide part 270 may guide the movement of the coupling member 263. Accordingly, the movement of the second body 230a and 230b is more stable.

Referring to FIGS. 9, 10, 14, and 15, after the circular knot of the medical wire is formed in the first mode, when the wire knot delivery device 200 is moved, the circular knot is moved to the part to be medically treated, as illustrated in FIG. 4.

After that, the second body 230a and 230b is moved to form the second mode, and then, the circular knot is tightened to fix tension of the medical wire.

The tightened knot may be cut without inserting a cutting mechanism into a deep portion of a blood vessel as the part to be medically treated. Referring to FIG. 14, points C1 and C2 of the wire knot delivery device 200 may be cutting points.

After the circular knot is appropriately tightened, the first rear string 211b may be cut at the point C1. After that, when one of two remaining strands of the first rear string 211b is held and pulled to the side B, the first catching part 213 is completely removed from the part to be medically treated (in operation E10).

In a same manner, after the second rear string 231b is cut at the point C2, when one of two remaining strands of the second rear string 231b is held and pulled to the side B, the second catching part 233 is completely removed from the part to be medically treated (in operation E20). Then, the wire knot delivery device 200 is removed to complete the medical treatment of the part.

After that, when a remaining part of the medical wire is unneeded, the remaining part may be cut and removed. When remaining part is needed, the remaining part may be left.

As described above, after the delivery of the circular knot of the medical wire is completed, it is unnecessary to insert the cutting mechanism for completing the medical treating of the part, into the deep portion of the blood vessel, and the medical treating of the part is safely and quickly completed using the cutting mechanism outside of a human body.

Referring to FIGS. 6, 8, 11, and 13, the wire knot delivery device 200 may further include a first handle part 281 attached to the first body 210a and 210b and having a hole through which a finger can be inserted. The hole of the first handle part 281 may have a size to allow a thumb to be inserted in the hole.

The wire knot delivery device 200 may further include a second handle part 283 attached to the second body 230a and 230b and having holes through which a finger can be inserted. The holes of the second handle part 283 may have a size to allow an index finger or a middle finger to be inserted in the hole.

The first and second handle parts 281 and 283 may further facilitate the forming of the first and second modes, by moving the second body 230a and 230b. When the thumb is inserted in the hole of the first handle part 281, and the index finger and the middle finger are inserted in the holes of the second handle part 283, the second body 230a and 230b may be moved relative to the first body 210a and 210b. In this case, an operator may use only one hand to move the second body 230a and 230b, which improves use convenience.

A wire knot delivery device according to the present invention includes a first body, a second body parallel to the first body and movably coupled to the first body, a first catching part connected to a side of the first body, and a second catching part connected to a side of the second body, thereby precisely adjusting tension of a medical wire and completing the adjustment.

In addition, the wire knot delivery device has a structure that decreases friction or resistance while delivering a knot of a medical wire, thus facilitating the delivery of the knot.

In addition, the wire knot delivery device adjusts a loop size of a knot of a medical wire while delivering the knot.

In addition, the wire knot delivery device finishes a medical procedure for forming a knot of a medical wire, without inserting a cutting mechanism into a deep part of a blood vessel after completing a delivery of the knot.

While all the embodiments and specified examples of the present disclosure have been particularly described to help those skilled in the art to understand the principles and concepts of the present invention, it will be understood by those skilled in the art that changes may be made therein without departing from the spirit and scope of the present invention. Thus, the disclosed embodiments should be considered in descriptive sense only and not for purposes of limitation. The scope of the present invention is defined not by the foregoing detailed description but by the appended claims, and all differences within the scope will be construed as being included in the present invention.

What is claimed is:

1. A wire knot delivery device for delivering and maintaining a knot of a medical wire, comprising:
   a first body comprising a first plate part, and a first through hole passing through the first plate part;
   a second body parallel to the first body and comprising a second plate part, and a second through hole passing through the second plate part, wherein the second body moves relative to the first body;
   a first loop connected to the first body and caught by a side of the knot;
   a second loop connected to the second body and caught by another side of the knot;

a coupling member head having a size that prevents the coupling member head from passing through the second through hole;

a coupling member rod extending from the coupling member head and inserted in the second through hole and the first through hole; and a coupling member threaded to an end part of the coupling member rod opposite to the coupling member head, wherein as the second body moves, a distance between the first loop and the second loop is adjusted.

2. The wire knot delivery device according to claim 1, further comprising a catheter tube which guides a movement of the second body such that the second body slides relative to the first body.

3. The wire knot delivery device according to claim 1, wherein the first loop is coupled to a first rear string routed through a first plate part of the first body; and the wire knot delivery device further comprises a first adjustment part coupled to the first plate part and configured to wind the first rear string, wherein the first adjustment part includes a first rotation member threaded to the first plate, and a first press member coupled to the first rotation member and configured to press the first rear string to a rotation shaft of the first rotation member.

4. The wire knot delivery device according to claim 1, wherein the loop is coupled to a second rear string routed through a second plate part of the second body; and the wire knot delivery device further comprises a second adjustment part coupled to the first plate part and configured to wind the second rear string, wherein the second adjustment part includes a second rotation member threaded to the first plate, and a second press member coupled to the second rotation member and configured to press the second rear string to a rotation shaft of the second rotation member.

5. The wire knot delivery device according to claim 1, wherein while the coupling member rod moves together with the second body, the coupling member rod is inserted in the second through hole, and the first through hole elongated in a moving direction of the second body guides movement of the coupling member rod.

6. The wire knot delivery device according to claim 5, wherein the coupling member moves together with the coupling member rod, and the wire knot delivery device further comprises an auxiliary guide part with a groove into which the movement of the coupling member is inserted so that the coupling member is guided by the auxiliary guide part.

7. The wire knot delivery device according to claim 1, further comprising a first handle part attached to the first body and having a hole.

8. The wire knot delivery device according to claim 1, further comprising a second handle part attached to the second body and having a hole.

9. A surgical method for delivering a knot of a medical wire, comprising:

preparing a wire knot delivery device, which includes a first body comprising a first plate part, and a first through hole passing through the first plate part, a second body parallel to the first body and comprising a second plate part, and second through hole passing through the second plate part and wherein the second body moves relative to the first body, a first catching part comprising a first catching part loop and connected to the first body, a second catching part comprising a second catching part loop and connected to a side of the second body, a coupling member head having a size to be prevented from passing through the second through hole, a coupling member rod extending from the coupling member head and inserted in the second through hole and the first through hole, and a coupling member coupled as a nut to an end part of the coupling member rod opposite to the coupling member head wherein as the second body moves, a distance between the first catching part and the second catching part is adjusted (operation S10), passing the medical wire through the first catching part loop and the second catching part loop (operation S20);

forming the knot by forming the medical wire into a circular shape (operation S30);

moving the knot to a part to be medically treated in the body of a patient, by moving the wire knot delivery device in a first mode that the first catching part loop and the second catching part loop are spaced apart from each other (operation S40);

adjusting tension of the medical wire by pulling the medical wire (operation S50); and forming a second mode that the first catching part loop and the second catching part loop are adjacent to each other, and tightening the knot of the medical wire (operation S60), wherein the first catching part has a string shape extending from the first plate part and forming the first catching part loop by bending and returning to a side of the first plate part, wherein the second catching part has a string shape extending from the second plate part and forming the second catching part loop by bending and returning to a side of the second plate part.

10. The surgical method according to claim 9, further comprising cutting and removing an unnecessary part of the medical wire (operation S70) after operation S60.

11. The surgical method according to claim 9, further comprising completely removing the first catching part from the part to be medically treated, by cutting the first catching part at a point C1 outside of the body of the patient and pulling the first catching part outside of the body of the patient (operation E10) after operation S60.

12. The surgical method according to claim 9, further comprising completely removing the second catching part from the part to be medically treated, by cutting the second catching part at a point C2 outside of the body of the patient and pulling the second catching part outside of the body of the patient (operation E20) after operation S60.

* * * * *